(12) United States Patent
Kataoka et al.

(10) Patent No.: US 7,202,068 B2
(45) Date of Patent: Apr. 10, 2007

(54) ENONE REDUCTASE AND METHODS OF MAKING AND USING THEREOF

(75) Inventors: Michihiko Kataoka, Kyoto-fu (JP); Sakayu Shimizu, Kyoto-fu (JP)

(73) Assignee: DSM IP Assets B.V., TE Heerlen (NL)

( * ) Notice: Subject to any disclaimer, the term of this patent is extended or adjusted under 35 U.S.C. 154(b) by 250 days.

(21) Appl. No.: 10/505,396

(22) PCT Filed: Feb. 14, 2003

(86) PCT No.: PCT/EP03/01473

§ 371 (c)(1), (2), (4) Date: Aug. 20, 2004

(87) PCT Pub. No.: WO03/070924

PCT Pub. Date: Aug. 28, 2003

(65) Prior Publication Data

US 2005/0106696 A1    May 19, 2005

(30) Foreign Application Priority Data

Feb. 22, 2002 (EP) ................................. 02003967

(51) Int. Cl.
*C12N 9/02* (2006.01)

(52) U.S. Cl. ..................................................... 435/189

(58) Field of Classification Search ................ 435/189, 435/183; 530/300, 350
See application file for complete search history.

(56) References Cited

FOREIGN PATENT DOCUMENTS

EP    1 074 630    2/2001

OTHER PUBLICATIONS

Kataoka, M. et al., "Old Yellow Enzyme from *Candida macedoniensis* Catalyzes the Stereospecific Reduction of the C=C Bond of Ketoisophorone," *Biosci. Biotechnol. Biochem.*, vol. 66, No. 12, pp. 2651-2657 (2002).

Wanner, P. and Tressl, R., "Purification and Characterization of Two Enone Reductases from *Saccharomyces cerevisiae*," *Eur. J. Biochem.*, vol. 255, pp. 271-278 (1998).

Wada, M. et al., "Production of a Doubly Chiral Compound, (4R,6R)-4-Hydroxy-2,2,6-Trimethylcyclohexanone, by Two-Step Enzymatic Asymmetric Reduction," *Applied and Environmental Microbiology*, vol. 69, No. 2, pp. 933-937 (2003).

*Primary Examiner*—Sandra E. Saucier
*Assistant Examiner*—Satyendra K. Singh
(74) *Attorney, Agent, or Firm*—Bryan Cave LLP

(57) ABSTRACT

An isolated enone reductase characterized by a molecular mass of 61300+/−5000 Da; NADPH and NADPH as cofactor; a temperature optimum of 55–60° C. at pH 7.4; a pH optimum of 4.5–8.5 and substrate specificity on $\alpha,\beta$-unsaturated ketones; a process for producing it from a microorganism and a process for producing levodione from ketoisophorone using such reductase.

19 Claims, No Drawings

ENONE REDUCTASE AND METHODS OF MAKING AND USING THEREOF

This application is the National Stage of International Application No. PCT/EP03/01473, filed Feb. 14, 2003.

The present invention relates to a novel enzyme involved in the production of (6R)-2,2,6-trimethyl cyclohexane-1,4-dione (hereinafter referred to as levodione) from 2,6,6-trimethyl-2-cyclohexene-1,4-dione (hereinafter referred to as ketoisophorone) and a process of producing said enzyme, wherein said enzyme is acting as an enone reductase. Levodione is an important intermediate in the synthesis of carotenoids, e.g. zeaxanthin.

A microbiological process of producing levodione from ketoisophorone has been known, see, e.g. U.S. Pat. No. 4,156,100.

The enzyme of the present invention belongs to the class of enone reductases and can be obtained from yeast, e.g. *Candida kefyr* or *Zygosaccharomyces rouxii*. The enzyme as isolated from *Candida kefyr* is both NADH and NADPH-dependent, with a molecular mass of 61.3 kDa under gel filtration chromatography. It consists of a single subunit of 45 kDa under denaturing electrophoretic conditions and shows an WV-visible absorption spectrum with peaks at 278,376 and 460 nm.

It is an object of the present invention to provide an isolated enone reductase having the following physico-chemical properties:
a) Molecular mass: 61,300±5,000 Da (Consisting of one subunit having a molecular mass of 45,000±5,000 Da)
b) Co-factor: NADPH and NADH
c) Substrate specificity: active on α,β-unsaturated ketones
d) Optimum temperature: 55–60° C. at pH 7.4
e) Optimum pH: 4.5–8.5.

As used herein, the term "enone reductase" encompasses proteins catalyzing the enzymatic reduction of carbonyl activated double bonds according to the Enzyme Nomenclature provided by the Nomenclature Committee of the International Union of Biochemistry and Molecular Biology (NC-IUBMB). It also relates to proteins having the above mentioned activities of an enone reductase, which proteins preferably catalyze the conversion of ketoisophorone into levodione.

More particularly, the present invention relates to isolated proteins having enone reductase activities as described above which are derived from a microorganism capable of producing said protein having the physico-chemical properties as described above.

The microorganisms used for the present invention are selected from yeast, including but not limited to microorganisms belonging to the genus *Candida* or *Zygosaccharomyces*, which are capable of producing enone reductase as defined hereinbefore. Functional equivalents, subcultures, mutants and variants of said microorganisms can also be used in the present invention.

In one embodiment of the present invention, the microorganism is a yeast, preferably *Candida*, more preferably *Candida kefyr*, and most preferably *Candida kefyr* (*Candida macedoniensis*) IFO 0960 or their functional equivalents, subcultures, mutants and variants thereof. The strain *Candida kefyr* (*Candida macedoniensis*) IFO 0960 is publicly available from and was deposited on Apr. 24, 2002 with the National Institute of Technology and Evaluation, Department of Biotechnology, 2-5-8 Kazusakamatari, Kisarazushi, Chiba, 292-0818 Japan under Deposit No.: NBRC 0960.

As used herein, the microorganisms "*Candida kefyr*" or "*Zygosaccharomyces rouxii*" also include synonyms or basonyms of such species having the same physico-chemical properties, as defined by the International Code of Nomenclature of Prokaryotes.

The enone reductase provided by the present invention can be prepared by cultivating an appropriate microorganism in an aqueous nutrient medium under aerobic conditions, disrupting the cells of the microorganism and isolating and purifying the enone reductase from the cell-free-extract of the disrupted cells of the microorganism.

It is thus another object of the present invention to provide a process for producing the enone reductase having the physico-chemical properties as defined above, which process comprises cultivating a microorganism, which is capable of producing the enone reductase having the above properties, in an aqueous nutrient medium under aerobic conditions, disrupting the cells of the microorganism and isolating and purifying the enone reductase from said cell extract.

Microorganisms used for the process of producing the enone reductase are those already defined above. In one embodiment of the present invention, the microorganism used for the production of enone reductase is a yeast, preferably *Candida*, more preferably *Candida kefyr*, and most preferably *Candida kefyr* (*Candida macedoniensis*) IFO 0960 or their functional equivalents, subcultures, mutants and variants thereof.

The enone reductase provided by the present invention is useful as a catalyst for the production of levodione from ketoisophorone. It is thus a still further object of the present invention to provide a process for producing levodione from ketoisophorone, which process comprises contacting ketoisophorone with (i) the enone reductase having the physico-chemical properties as defined above in the presence of NADH or NADPH, (ii) the cells or the cell-free extract of said microorganism capable of producing the enzyme as defined in (i), and in each of the cases isolating the resulting levodione from the reaction mixture.

In one embodiment, the microorganism being capable of producing the enzyme as defined above and which is used for the production of levodione is a yeast, preferably *Candida*, more preferably *Candida kefyr*, and most preferably *Candida kefyr* (*Candida macedoniensis*) IFO 0960 or their functional equivalents, subcultures, mutants and variants thereof.

The microorganism may be cultured in a nutrient medium containing saccharides such as glucose or sucrose, alcohols such as ethanol or glycerol, fatty acids such as oleic acid, stearic acid or esters thereof, or oils such as rape-seed oil or soybean oil as carbon sources; ammonium sulfate, sodium nitrate, peptone, amino acids, corn steep liquor, bran, yeast extract and the like as nitrogen sources; magnesium sulfate, sodium chloride, calcium carbonate, potassium monohydrogen phosphate, potassium dihydrogen phosphate and the like as inorganic salt sources; and malt extract, meat extract and the like as other nutrient sources. The cultivation can be carried out aerobically, normally within a period of 1 to 7 days at a medium pH of 3 to 9 and a cultivation temperature of 10 to 40° C. More preferably, the cultivation period is between 2 and 4 days, the medium pH is between 5 and 8, and the cultivation temperature is between 25 and 35° C.

In the following, an embodiment for isolation and purification of the enone reductase from the microorganism after the cultivation is briefly described:
(1) Cells are harvested from the liquid culture broth by centrifugation or filtration,
(2) the harvested cells are washed with water, physiological saline or a buffer solution having an appropriate pH;

(3) the washed cells are suspended in the buffer solution and disrupted by means of a homogenizer, sonicator, French press or treatment with lysozyme and the like to give a solution of disrupted cells; and (4) the enone reductase is isolated and purified from the cell-free extract of the disrupted cells.

The reaction can be conducted at pH values of from about 4.5 to about 8.5 in the presence of NADH or NADPH in a solvent, such as Tris-HCl buffer, phosphate buffer and the like. One embodiment of the present invention is related to the process for producing levodione from ketoisophorone using the enone reductase or a microorganism as defined above, wherein the reaction is conducted at a pH in the range of from 4.5 to 8.5, preferably in the range of from 5.0 to 8.0.

A further aspect of the present invention is related to the process for producing levodione from ketoisophorone using the enone reductase or a microorganism as defined above, wherein the temperature of the reaction is in the range of from 30 to 60° C., preferably in the range of from 55 to 60° C.

When the pH and the temperature are set at 5.0 to 8.0 and 45 to 60° C., respectively, the reaction usually produces the best results. Preferably, the pH is in the range of from 5.0 to 8.0 and the temperature is in the range of from 55 to 60° C.

The concentration of ketoisophorone in a solvent can vary depending on other reaction conditions, but, in general, is between 1 mM and 2 M, preferably between 10 mM and 100 mM.

In the reaction, the enone reductase may also be used in an immobilized state with an appropriate carrier. Any means of immobilizing enzymes generally known in the art may be used. For instance, the enzyme may be bound directly to a membrane, granules or the like of a resin having one or more functional groups or it may be bound to the resin through bridging compounds having one or more functional groups, e.g. glutaraldehyde.

The present invention is not only directed to the isolation of enzymes having enone reductase activity as described above, but also to the cloning of the corresponding genes encoding such enzymes using methods known in the art. The cDNA of such cloned genes might be useful for the introduction into a suitable expression vector, which is then introduced into a host cell, e.g. such as E. coli or yeasts. The recombinant proteins are useful for the conversion of ketoisophorone to levodione, an important intermediate step in the production of carotenoids such as actinol or zeaxanthin.

The physico-chemical properties of the purified sample of the enone reductase prepared according to the Examples mentioned hereinafter are as follows:

1) Enzyme Activity

The novel enone reductase of the present invention catalyzes the reduction of ketoisophorone to levodione in the presence of a co-factor according to the following formula:

The standard enzyme assay was performed as follows: a total volume of 1 ml of the basal reaction mixture (200 μl of 1 M Tris-HCl buffer pH 7.5, 100 μl of 80 mM NADH or NADPH, 100 μl of 0.658 M ketoisophorone, 600 μl H$_2$O) was supplemented by 5 μl of the enzyme solution and incubated at 40° C. One unit of the enzyme activity was defined as the amount of the enzyme, which catalyzes the oxidation of 1 μmol of ketoisophorone per minute. The reaction mixture was extracted by 1 ml of ethylacetate to recover the levodione into the ethylacetate layer. The extract was analyzed by gas chromatography [column: ULBON HR-20M (Shinwa, Japan) 0.25 mmφ×30 m, column temperature: 160° C. (constant), injector temperature: 250° C., carrier gas: He (ca. 1 ml/min)]. The protein concentration was determined by using a Bio-Rad protein assay kit (Bio-Rad, USA).

2) Molecular Weight

The molecular weight (MW) of the protein was measured with a gel filtration column Superdex 200 (Amersham Biosciences AB, SE-751 84 Uppsala, Sweden). The apparent molecular mass of the enzyme was calculated to be 61,300±5,000 Da in comparison with the molecular weight marker proteins (Boehringer Mannheim Biochemica; Germany) ferritin (molecular mass: 450,000 Da), catalase (molecular mass: 240,000 Da), aldolase (molecular mass: 158,000 Da), bovine serum albumin (molecular mass: 68,000 Da), ovalbumin (molecular mass: 45,000 Da), chymotrypsinogen (molecular mass: 25,000 Da) and cytochrome c (molecular mass: 12,500 Da). SDS-polyacrylamide gel electrophoresis (SDS-PAGE) gave a single band with a molecular weight of 45,000±5,000 Da in comparison with the molecular weight marker proteins (Amersham Biosciences AB) phosphorylase b (molecular mass: 97,000 Da), bovine serum albumin (molecular mass: 66,300 Da), ovalbumin (molecular mass: 42,400 Da), carbonic anhydrase (molecular mass: 30,000 Da), and soybean trypsin inhibitor (molecular mass: 20,100 Da). This indicates that the enzyme is composed of one subunit.

3) Co-factor

The cofactor requirement of the enzyme to convert ketoisophorone to levodione was investigated. As a result, NADH and NADPH could serve as a co-factor for this reductive reaction.

3) Substrate Specificity

Substrate specificity of the enzyme was determined by using the same enzyme assay method as described above under (1), except that various substrate solutions (0.05% final concentration in the reaction mixture) were used instead of ketoisophorone, and the reaction was done at 30° C. The relative activity (%) of different substrates is compared in Table 1, showing the best result with 3-butene-2-one.

TABLE 1

| Substrate | Relative Activity (%) |
| --- | --- |
| Ketoisophorone | 100 |
| 2-Cyclohexen-1-one | 252.1 |
| 3-Butene-2-one | 403.3 |
| R-(−)-Carvone | 56.3 |
| Cinnamaldehyde | 216.7 |
| 1-Nitro-1-cyclohexen | 373.8 |

5) Optimum Temperature

The enzyme activities were measured at temperatures from 20 to 70° C. by using the same enzyme assay method as described above under (1), except that 2-cyclohexen-1-one was a substrate. As summarized in Table 2, the optimum temperature of the enzyme activity was 55–60° C.

TABLE 2

| Temperature (° C.) | Relative Activity (%) |
|---|---|
| 20 | 12.7 |
| 25 | 22.5 |
| 30 | 32.2 |
| 35 | 40.5 |
| 40 | 48.6 |
| 45 | 64.2 |
| 50 | 68.1 |
| 55 | 97.5 |
| 60 | 100 |
| 65 | 30 |
| 70 | 10.3 |

5) Optimum pH

The correlation between the enzyme activity and the pH values of the reaction mixture was determined by using the same enzyme assay method as described above under (1), except that various pHs and buffers were used and 0.05% (final concentration) 2-cyclohexen-1-one was used as a substrate. The optimum pH of the enzyme reaction was 4.5–8.5, as shown in Table 3.

TABLE 3

| Buffer | pH | Enzyme activity (Unit/ml) |
|---|---|---|
| Sodium acetate | 4.0 | 7.7 |
| | 4.5 | 13.1 |
| | 5.0 | 11.8 |
| | 5.5 | 8.5 |
| Potassium phosphate | 5.5 | 11.2 |
| | 6.0 | 10.4 |
| | 6.5 | 10.9 |
| | 7.0 | 10.9 |
| | 7.5 | 9.6 |
| Tris-HCl | 7.5 | 11.3 |
| | 8.0 | 11.3 |
| | 8.5 | 11.8 |
| | 9.0 | 10.2 |
| Glycine-NaOH | 8.5 | 10.7 |
| | 9.0 | 8.7 |
| | 9.5 | 8.9 |
| | 10.0 | 8.1 |
| | 10.5 | 4.2 |

7) Effect of Metal Ions and Other Compounds

Effects of metal ions and other compounds on the enzyme activity were investigated by using the same enzyme assay method as described above under (1), except that 2-cyclohexen-1-one was used as a substrate, and various metals and other compounds were added to the reaction mixture, where the final concentration of metal was 1 mM. Pb ions and trypanoflavine inhibited the enzyme activity strongly. Ions of Ag, Hg, Cu, V and guanidine inhibited the enzyme activity moderately. The results are depicted in Table 4.

TABLE 4

| Metal or other compounds | Relative Activity (%) |
|---|---|
| None | 100 |
| LiCl | 104 |
| NaCl | 108 |
| KCl | 103 |
| RbCl | 107 |
| AgNO$_3$ | 49.1 |
| CaCl$_2$ | 108 |
| MnCl$_2$ | 94.6 |
| BeSO$_4$ | 80.9 |
| CdCl$_2$ | 104 |
| MgCl$_2$ | 111 |
| CoCl$_2$ | 113 |
| HgCl$_2$ | 40.8 |
| ZnSO$_4$ | 101 |
| CuSO$_4$ | 55.9 |
| NiCl | 108 |
| Pb(NO$_3$)$_2$ | 0 |
| NH$_4$VO$_3$ | 9.6 |
| Guanidine | 61.1 |
| Trypaflavine | 0 |
| Thiourea | 96.0 |
| Iodoacetate | 93.6 |
| NaSCN | 93.6 |
| Hydrazine | 108 |
| NaF | 101 |
| KCN | 91.8 |
| EDTA | 110 |

8) Purification Procedure

The purification of the enone reductase may, in principle, be effected by any combination of known purification methods, such as fractionation with precipitants. e.g. ammonium sulfate, polyethylene glycol and the like, ion exchange chromatography, adsorption chromatography, gel-filtration chromatography, gel electrophoresis and salting out and dialysis.

The following Examples further illustrate the present invention.

EXAMPLE 1

Preparation of the Enone Reductase

All operations were performed at 4° C. in 20 mM Tris-HCl buffer (pH 7.0) unless otherwise stated.

(1) Cultivation of *Candida kefyr* (*Candida macedoniensis*) IFO 0960

*Candida kefyr* (*Candida macedoniensis*) IFO 0960 grown on an agar plate was inoculated into 5 ml of the medium (pH 6.0) consisting of D-glucose (5%), peptone (0.5%), KH$_2$PO$_4$ (0.2%), K$_2$HPO$_4$ (0.1%), MgSO$_4$.7H$_2$O (0.02%) and yeast extract (0.1%) in a tube, and incubated for 2 days at 28° C. 10 ml of the seed culture thus prepared were inoculated into 500 ml of the same medium as above in 2 l Sakaguchi-flasks, and incubated for 2 days at 28° C. 5 liters of the culture from 10 flasks thus prepared were centrifuged at 8,000 rpm for 20 minutes at 4° C. In total, 60.5 g of wet cells were obtained.

(2) Preparation of the Cell-free Extract

The wet cells (60.5 g) were suspended in 121 ml of the buffer, and sonicated for 2 hours with the power of 190 W by using Kubota Insonator 201 sonicator (Kubota, Japan). After sonication, the sample was centrifuged at 10,000 rpm for 20 minutes. As a result, 139 ml of the cell-free extract containing 1,550 mg of protein was obtained.

(3) Ammonium Sulfate Precipitation

The cell-free extract (80 ml) obtained in the previous step was fractionated with solid ammonium sulfate. The 40–80% fraction (78.5 ml) was dialyzed against 5 l of the buffer for 4 times, and 91 ml of the dialyzed solution was obtained.

(4) Diethylaminoethyl-Sephacel Column Chromatography

The dialyzed sample prepared above was applied to a diethylaminoethyl (DEAE)-Sephacel column (2.5 cm in diameter and 14 cm in height; Amersham Biosciences AB, Sweden) which was equilibrated with the buffer. After washing the column with 200 ml of the same buffer, the enzyme was eluted with 530 ml of a linear gradient of NaCl (0–0.6 M). The enzyme activity was eluted with 0.1 M NaCl.

(5) Phenyl-Superose HR10/10 Column Chromatography

The sample from the previous step was supplemented by NaCl to give a final concentration of 4 M. The column (1 cm in diameter×30 cm in length; Amersham Biosciences AB, Sweden) was equilibrated with the buffer containing 4 M NaCl, and applied to the above sample. The enzyme was eluted by a 160 ml of linear gradient of the buffer (4–0 M NaCl). The enzyme activity was eluted at an NaCl concentration of 2 M.

(6) Superdex 200 HR10/30 Column Chromatography

The sample from the previous step was applied to a Superdex 200 HR10/30 column (1 cm in diameter×30 cm in length; Amersham Biosciences AB, Sweden) chromatography. The column was equilibrated with the buffer containing 2 M NaCl, and developed. Fractions having the enzyme activity were collected. A summary of the purification steps of the enzyme is shown in Table 5.

TABLE 5

| Step | Total Activity (milli unit) | Total Protein (mg) | Specific Activity (milli unit/mg) | Purification (-fold) |
|---|---|---|---|---|
| Cell-free extract | 1450 | 1550 | 0.934 | 1 |
| $(NH4)_2SO_4$ treatment | 1560 | 664 | 2.34 | 2.51 |
| DEAE Sephacel | 933 | 65.7 | 14.2 | 15.2 |
| Pheny Superose | 874 | 17.1 | 51.2 | 54.8 |
| Superdex 200 | 783 | 15.3 | 51.3 | 54.9 |

(7) Identification of the Reaction Product

The reaction mixture (1 ml) consisting of 10 mg/ml of ketoisophorone, 0.6 mg/ml of $NADP^+$, 0.2 mg/ml of glucose dehydrogenase (Amano Enzyme, Japan), and 50 mg/ml of D-glucose in 50 mM Tris-HCl (pH 7.5) buffer was supplemented by 50 milli units of the enzyme from the fraction of Superdex 200 of Table 5. After incubation at 28° C. for 24 hours, the mixture was extracted with 1 ml of ethylacetate. The extract was analyzed by gas chromatography. The product was identified to be levodione in comparison with the standard sample of levodione.

What is claimed is:

1. An isolated enone reductase having the following physico-chemical properties:
    a) Molecular mass: 61,300±5,000 Da as determined by gel filtration,
    b) Co-factor: NADPH and NADH,
    c) Substrate specificity: active on α, β-unsaturated ketones,
    d) Optimum temperature: 55–60° C. at pH 7.4,
    e) Optimum pH: 4.5–8.5, and
    f) A single subunit having a molecular mass of 45,000±5,000 Da as determined by SDS-polyacrylamide gel electrophoresis.

2. The enone red uctase according to claim 1, which is derived from a microorganism which is capable of producing the enone reductase having the properties as defined in claim 1.

3. The enone reductase according to claim 2, wherein the microorganism is a yeast.

4. The enone reductase according to claim 2, wherein the microorganism is *Candida kefyr* IFO 0960, its functional equivalents, subcultures, mutants or variants.

5. A process for producing an enone reductase having the following physico-chemical properties:
    a) Molecular mass: 61,300±5,000 Da as determined by gel filtration,
    b) Co-factor: NADPH and NADH,
    c) Substrate specificity: active on α, β-unsaturated ketones,
    d) Optimum temperature: 55–60° C. at pH 7.4,
    e) Optimum pH: 4.5–8.5, and
    f) A single subunit having a molecular mass of 45.000±5,000 Da as determined by SDS-polyacrylamide gel electrophoresis,
which process comprises cultivating a microorganism, which is capable of producing the enone reductase having the above properties, in an aqueous nutrient medium under aerobic conditions, disrupting the cells of the microorganism, and isolating and purifying the enone reductase from said extract.

6. The process according to claim 5, wherein the microorganism is a yeast.

7. A process for producing levodione from ketoisophorone which process comprises contacting ketoisophorone with
    (i) an enone reductase having the following physico-chemical properties:
        a) Molecular mass: 61,300±5,000 Da as determined by gel filtration.
        b) Co-factor: NADPH and NADH,
        c) Substrate specificity: active on α, β-unsaturated ketones,
        d) Optimum temperature: 55–60° C. at pH 7.4,
        e) Optimum pH: 4.5–8.5 and
        f) A single subunit having a molecular mass of 45.000±5,000 Da as determined by SDS-polyacrylamide gel electrophoresis,
    in the presence of NADH or NADPH; or
    (ii) cells or a cell-free extract of a microorganism belonging to the genus *Candida* capable of producing the enzyme as defined in (i),
and isolating the resulting levodione from the reaction mixture.

8. The process according to claim 7, wherein the microorganism is a yeast.

9. The process according to claim 7, wherein the reaction is conducted at a pH in the range of from 4.5 to 8.5.

10. The process according to claim 7, wherein the temperature of the reaction is in the range of from 30 to 6000.

11. The process according to claim 8, wherein the reaction is conducted at a pH in the range of from 4.5 to 8.5.

12. The process according to claim 8, wherein the temperature of the reaction is in the range of from 30 to 60° C.

13. The process according to claim 9, wherein the temperature of the reaction is in the range of from 30 to 60° C.

14. The process according to claim 11, wherein the temperature of the reaction is in the range of from 30 to 60° C.

15. The enone reductase according to claim 4, wherein the microorganism is *Candida kefyr* IFO 0960.

16. The process according to claim 5, wherein the microorganism is *Candida kefyr* IFO 0960, its functional equivalents, subcultures, mutants or variants.

17. The process according to claim 6, wherein the microorganism is *Candida kefyr* IFO 0960, its functional equivalents, subcultures, mutants or variants.

18. The process according to claim 7, wherein the microorganism is *Candida kefyr* IFO 0960, its functional equivalents, subcultures, mutants or variants.

19. The process according to claim 8, wherein the microorganism is *Candida kefyr* IFO 0960, its functional equivalents, subcultures, mutants or variants.

* * * * *